United States Patent [19]
Lal

[11] Patent Number: 6,096,922
[45] Date of Patent: Aug. 1, 2000

[54] PROCESS FOR THE SYNTHESIS OF DIALKYL, DIARYL, AND ARYLALKYL AMINOSULFUR TRIFLUORIDES

[75] Inventor: Gauri Sankar Lal, Whitehall, Pa.

[73] Assignee: Air Products and Chemicals, Inc., Allentown, Pa.

[21] Appl. No.: 09/432,724

[22] Filed: Nov. 1, 1999

[51] Int. Cl.[7] .................................................. C07C 303/00
[52] U.S. Cl. ............................................................ 562/822
[58] Field of Search ............................. 564/102; 562/822

[56] References Cited

U.S. PATENT DOCUMENTS

| 1,864,289 | 6/1932 | Anglemyer et al. | 96/330 |
| 3,976,691 | 8/1976 | Middleton | 260/544 F |
| 5,763,728 | 9/1998 | Kocal et al. | 585/724 |

OTHER PUBLICATIONS

Middleton, "New Fluorinating Reagents. Dialkylaminosulfur Fluorides" J. Org. Chem., vol. 40, No. 5, 1975.
Wiechert, "Amine–Poly(Hydrogen Fluoride) Solid Complexes" Chem. Eur. J. 1998, 4, No. 6.

*Primary Examiner*—Peter O'Sullivan
*Attorney, Agent, or Firm*—Geoffrey L. Chase

[57] ABSTRACT

A process for synthesizing an aminosulfur trifluoride is provided. The process includes reacting a secondary amine with $SF_4$ to produce the aminosulfur trifluoride product and a liquid amine-HF adduct. Substantially no solid amine-HF adduct is produced in the one-step reaction of the process. The reaction is conducted in a reaction solvent containing a tertiary amine. The process produces aminosulfur trifluorides, such as dialkyl, diaryl and arylalkyl aminosulfur trifluorides, in high yields.

17 Claims, No Drawings

PROCESS FOR THE SYNTHESIS OF DIALKYL, DIARYL, AND ARYLALKYL AMINOSULFUR TRIFLUORIDES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The invention generally relates to methods for synthesizing aminosulfur trifluorides and more particularly to methods for synthesizing dialkyl, diaryl, and arylalkyl aminosulfur trifluorides.

In view of the importance of organo-fluorine compounds in the pharmaceutical and agrochemical industries, efforts aimed at the development of simple, safe, and efficient methods for their synthesis have escalated in recent years. The conversion of carbon-oxygen to carbon-fluorine bonds by nucleophilic fluorinating sources (deoxofluorination) represents one such technique which has been widely used for the selective introduction of fluorine into organic molecules. This transformation has been accomplished routinely with dialkylaminosulfur trifluorides, such as DAST ($NEt_2SF_3$) and more recently with bis(2-methoxyethyl) aminosulfur trifluoride.

Middleton, 40(5) *J. Org. Chem.* 574 (1975), describes a process for obtaining dialkylaminosulfur trifluorides, such as DAST, in a two-step process starting from a secondary amine. The amine is silylated with trimethyl silyl chloride or hexamethyl disilazane. After isolation, the silylated amine is reacted with sulfur tetrafluoride to obtain the trifluoride.

As a two-step process, the Middleton process is typically carried out in two reaction vessels. In addition, the process requires the isolation of a pure intermediate, adding to the complexity and cost of the process.

SU Patent No. 1864289 (Markovskii et. al.) describes a more concise process for preparing dialkylaminosulfur trifluorides, as well as an arylalkyl aminosulfur trifluoride. Markovskii et al. prepared aminosulfur trifluorides in a one-step reaction by reacting the corresponding secondary amine with sulfur tetrafluoride in the presence of an amine base that produces a solid amine-HF adduct. This adduct is filtered to obtain the trifluoride in solution of the reaction solvent. Unfortunately, it is difficult to cleanly remove the solid amine-HF adduct from the product because small particles of adduct can escape the filter. In addition, a small amount of adduct is soluble in the reaction solvent and is retained in the product after filtration and evaporation of the solvent.

Accordingly, it is desired to provide a method for producing aminosulfur trifluorides which does not suffer from the aforementioned deficiencies of prior art methods.

All references cited herein are incorporated herein by reference in their entireties.

BRIEF SUMMARY OF THE INVENTION

The invention addresses at least the foregoing deficiencies of the prior art by providing a process for synthesizing an aminosulfur trifluoride, said process comprising reacting a secondary amine with $SF_4$ under conditions such that said aminosulfur trifluoride and a liquid amine-HF adduct are produced. Substantially no solid amine-HF adduct is produced in the one-step reaction of the process. The reaction is conducted in a reaction solvent containing a tertiary amine. The process produces aminosulfur trifluorides, such as dialkyl, diaryl and arylalkyl aminosulfur trifluorides, in high yields.

BRIEF DESCRIPTION OF SEVERAL VIEWS OF THE DRAWINGS

Not applicable.

DETAILED DESCRIPTION OF THE INVENTION

The present invention provides a process for the synthesis of aminosulfur trifluorides, such as, e.g., dialkyl, diaryl and arylalkyl aminosulfur trifluorides. The process involves reacting a secondary amine with $SF_4$ in the presence of a tertiary amine to produce the aminosulfur trifluoride and a liquid amine-HF adduct, which is immiscible in the reaction solution containing the aminosulfur trifluoride. The adduct separates out as a heavy layer, thus providing for the facile separation from the reaction product mixture.

Unlike certain prior art processes, embodiments of the inventive process can be carried out in one reaction vessel which makes it more convenient and less expensive for industrial utility. Another economic advantage is that the process does not require the isolation of a pure intermediate. Furthermore, because a liquid amine-HF adduct rather than a solid HF-adduct is produced, a greater product yield is obtained. This is because in the prior art process it is difficult to cleanly remove the solid HF-adduct from the product owing to retention of small particles of adduct which can escape the filter. In addition, a small amount of adduct is soluble in the reaction solvent and is retained in the product after filtration and evaporation of the solvent.

In the inventive process, the secondary amine is reacted with $SF_4$ in a solvent containing the tertiary amine. The insoluble liquid is separated. After removal of the solvent (preferably by distillation), the product is preferably redissolved into a less polar extraction solvent to remove residual amine-HF adduct. Separation of the latter followed by distillation affords the pure aminosulfur trifluoride.

Preferred secondary amines include dialkyl, diaryl and aryl alkyl amines.

Suitable tertiary amines produce a liquid amine-HF adduct at a temperature ranging from −78° C. to the boiling point of the reaction solvent. Preferred tertiary amines include trimethylamine, ethyl dimethylamine, N-methylpyrrolidine, tripropylamine, tributylamine, tripentylamine, trihexylamine, N-methyl-N-propyl-N-butylamine, and N-ethyl-N-isopropyl-N-butylamine.

The reaction solvent is any solvent which will not react with $SF_4$ or the aminosulfur trifluoride product of the process and which will not dissolve the amine-HF adduct. Preferred reaction solvents include organics, such as dialkyl ethers, hydrocarbons, and halogenated hydrocarbons. A particularly preferred reaction solvent is methyl-t-butylether (MTBE).

The extraction solvent used for extraction is any solvent which will selectively dissolve the trifluoride over the amine-HF adduct, e.g., organics, such as alkanes and alkenes. Preferred extraction solvents include pentane and hexane.

The invention will be illustrated in more detail with reference to the following examples, but it should be understood that the present invention is not deemed to be limited thereto.

EXAMPLE 1
Diethylaminosulfur trifluoride using N-methylpyrrolidine as HF scavenger A solution of N-methylpyrrolidine (12.77 g, 150 mmol) in methyl-t-butyl ether (100 mL) was charged into a 300 mL Parr reactor equipped with a magnetic stirring shaft, and via swage connections one port was attached to a 100 mL pressure equalized dropping funnel. The reactor was connected by a $N_2$ inlet tube, and a $SF_4$ gas inlet tube to a metal vacuum line manifold which was in turn attached to a $SF_4$ cylinder, a 1 L stainless steel ballast equipped with a pressure gauge, a soda-lime trap and a vacuum pump. The reactor was cooled to −30° C. with a dry ice/acetone bath. The 1 L ballast in the manifold was filled with $SF_4$ from a gas cylinder to produce a pressure of $SF_4$ of 52.2 psia (150 mmol). The reactor was evacuated in vacuo and the $SF_4$ was introduced into it slowly. A solution of diethylamine (10.95 g, 150 mmol) in methyl-t-butyl ether (25 mL) from the dropping funnel was slowly added to the solution. After stirring for 30 min, the excess $SF_4$ was pumped out of the solution through the soda-lime trap and the reactor was filled with $N_2$ to approximately atmospheric pressure (~15 psi). The lower layer was separated and the solution was evaporated in vacuo. The residue was dissolved into 20 mL of pentane and the lower layer was again separated. The solvent was evaporated to afford 15.2 g (63% yield) of product.

EXAMPLE 2
Diphenylaminosulfur trifluoride using N-methylpyrrolidine as HF scavenger Diphenylaminosulfur trifluoride was prepared as described above by reacting diphenylamine (150 mmol, 25.35 g) with $SF_4$ (150 mmol) in methyl-t-butyl ether in the presence of N-methylpyrrolidine (12.77 g, 150 mmol). Work up as above afforded 29.68 g (77% yield) of product. H NMR (CDCl$_3$) d 7.5–7.3 (m, 10H), F (CDCl$_3$) d 69.5 (d, 2F), 31 (t, IF).

EXAMPLE 3
N-methyl-N-phenylaminosulfur trifluoride using N-methylpyrrolidine as HF scavenger N-methyl-N-phenylaminosulfur trifluoride was obtained as above by reacting N-methylaniline (16.05 g, 150 mmol) with $SF_4$ (150 mmol) in methyl-t-butyl ether in the presence of N-methylpyrrolidine (12.77 g, 150 mmol). Work up as above afforded 15.60 g (80% yield) of product. H NMR (CDCl$_3$) d 7.5–7.3 (m, 3H), 7.3–7.0 (m, 2H) 3.4 (s, 3H). F (CDCl$_3$) d 64 (d, 2F), 26 (t, 1 F).

EXAMPLE 4
Bis(2-methoxyethyl)aminosulfur trifluoride using N-methylpyrrolidine as HF scavenger Bis(2-methoxyethyl)aminosulfur trifluoride was obtained as above by reacting bis(2-methoxyethyl)amine (19.95 g, 150 mmol) with $SF_4$ (150 mmol) in methyl-t-butyl ether in the presence of N-methylpyrrolidine (12.77 g, 150 mmol). Work up as above afforded 24.86 g (75% yield) of product. H NMR (CDCl$_3$) d 3.5 (t, 4H), 3.15 (t, 4H) 3.05 (s, 6H). F (CDCl$_3$) d 55 (s, br, 2F), 28 (s, br, 1F).

EXAMPLE 5
Bis(2-methoxyethyl)aminosulfur trifluoride using trimethylamine as HF scavenger Bis(2-methoxyethyl)aminosulfur trifluoride was obtained as above by reacting bis(2-methoxyethyl)amine (19.95 g, 150 mmol) with $SF_4$ (150 mmol) in methyl-t-butyl ether in the presence of trimethylamine (8.87 g, 150 mmol). Work up as above afforded 26.52 g (80% yield) of product. H NMR (CDCl$_3$) d 3.5 (t, 4H), 3.15 (t, 4H) 3.05 (s, 6H). F (CDCl$_3$) d 55 (s, br, 2F), 28 (s, br,1 F).

EXAMPLE 6
Bis(2-methoxyethyl)aminosulfur trifluoride using N,N-dimethylethylamine as HF scavenger Bis(2-methoxyethyl)aminosulfur trifluoride was obtained as above by reacting bis(2-methoxyethyl)amine (19.95 g, 150 mmol) with $SF_4$ (150 mmol) in methyl-t-butyl ether in the presence of N,N-dimethylethylamine (10.97 g, 150 mmol). Work up as above afforded 26.52 g (80% yield) of product. H NMR (CDCl$_3$) d 3.5 (t, 4H), 3.15 (t, 4H) 3.05 (s, 6H). F (CDCl$_3$) d 55 (s, br, 2F), 28 (s, br, 1 F).

The examples are summarized in Table 1, below.

TABLE 1

Preparation of aminosulfur trifluorides $$R_2NH\ (l) + SF_4\ (g) \xrightarrow[\text{solvent}]{R'_3N\ (l)} R_2NSF_3\ (l) + R'_3N \cdot HF\ (l)$$

| Starting 2° amine | 3° amine (HF scavenger) | Product (% yield) | Physical state of amine·HF adduct at 25° C. |
|---|---|---|---|
| (C$_2$H$_5$)$_2$NH | Et$_3$N | 58 | solid |
| (MeOCH$_2$CH$_2$)$_2$NH | Et$_3$N | 65 | solid |
| (C$_2$H$_5$)$_2$NH | N-methylpyrrolidine | 63 | liquid |
| Ph$_2$NH | N-methylpyrrolidine | 77 | liquid |
| PhNHMe | N-methylpyrrolidine | 80 | liquid |
| (MeOCH$_2$CH$_2$)$_2$NH | N-methylpyrrolidine | 75 | liquid |
| (MeOCH$_2$CH$_2$)$_2$NH | Me$_3$N | 80 | liquid |
| (MeOCH$_2$CH$_2$)$_2$NH | Me$_2$NEt | 80 | liquid |

While the invention has been described in detail and with reference to specific examples thereof, it will be apparent to one skilled in the art that various changes and modifications can be made therein without departing from the spirit and scope thereof.

SEQUENCE LISTING

Not applicable.

What is claimed is:

1. A process for synthesizing an aminosulfur trifluoride, said process comprising reacting a secondary amine with $SF_4$ under conditions such that said aminosulfur trifluoride and a liquid amine-HF adduct are produced.

2. The process of claim 1, wherein substantially no solid amine-HF adduct is produced.

3. The process of claim 2, wherein said reacting is a one-step reaction.

4. The process of claim 1, wherein said reacting is conducted in a reaction solvent containing a tertiary amine.

5. The process of claim 4, wherein said tertiary amine is selected from the group consisting of trimethylamine, ethyl dimethylamine, N-methylpyrrolidine, tripropylamine, tributylamine, tripentylamine, trihexylamine, N-methyl-N-propyl-N-butylamine and N-methyl-N-isopropyl-N-butylamine.

6. The process of claim 5, wherein said secondary amine is selected from the group consisting of dialkyl amine, diaryl amine and arylalkyl amine.

7. The process of claim 1, wherein said secondary amine is selected from the group consisting of dialkyl amine, diaryl amine and arylalkyl amine.

8. The process of claim 4, wherein said reaction solvent does not react with $SF_4$ or said aminosulfur trifluoride and does not dissolve the amine-HF adduct.

9. The process of claim 4, wherein said reaction solvent is selected from the group consisting of dialkyl ethers, hydrocarbons and halogenated hydrocarbons.

10. The process of claim 4, wherein said solvent is methyl-t-butylether.

11. The process of claim 4, further comprising purifying insoluble aminosulfur trifluoride product liquid by distillation.

12. The process of claim 4, further comprising separating residual amine-HF adduct heavier layer by distillation.

13. The process of claim 4, further comprising redissolving insoluble aminosulfur trifluoride product liquid in an extraction solvent to remove residual amine-HF adduct, wherein said extraction solvent is less polar than said reaction solvent and selectively dissolves said aminosulfur trifluoride over said amine-HF adduct.

14. The process of claim 13, wherein said extraction solvent is an organic solvent.

15. The process of claim 13, wherein said extraction solvent is an alkane or an alkene.

16. The process of claim 13, wherein said extraction solvent is pentane.

17. The process of claim 13, wherein said extraction solvent is hexane.

* * * * *